United States Patent
Lee et al.

(10) Patent No.: US 9,828,403 B2
(45) Date of Patent: Nov. 28, 2017

(54) METALLOCENE COMPOUNDS, CATALYST COMPOSITIONS COMPRISING THE SAME, AND METHOD FOR PREPARING OLEFIN POLYMERS USING THE SAME

(71) Applicant: LG CHEM, LTD., Seoul (KR)

(72) Inventors: Sung Min Lee, Daejeon (KR); Ki Soo Lee, Daejeon (KR); Heon Yong Kwon, Daejeon (KR); Dae Sik Hong, Daejeon (KR); Se Young Kim, Daejeon (KR); Yong Ho Lee, Daejeon (KR); Eun Young Shin, Daejeon (KR); Sung Ho Park, Daejeon (KR); Min Seok Cho, Daejeon (KR); Kyung Jin Cho, Daejeon (KR); Jin Young Park, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 15/037,483

(22) PCT Filed: Aug. 12, 2015

(86) PCT No.: PCT/KR2015/008457
§ 371 (c)(1),
(2) Date: May 18, 2016

(87) PCT Pub. No.: WO2016/024818
PCT Pub. Date: Feb. 18, 2016

(65) Prior Publication Data
US 2016/0297843 A1    Oct. 13, 2016

(30) Foreign Application Priority Data

Aug. 12, 2014  (KR) .................... 10-2014-0104498
Aug. 11, 2015  (KR) .................... 10-2015-0113460

(51) Int. Cl.
| | | |
|---|---|---|
| C07F 17/00 | (2006.01) | |
| C08F 4/6592 | (2006.01) | |
| C08F 10/00 | (2006.01) | |
| C08F 4/659 | (2006.01) | |
| C08F 110/02 | (2006.01) | |

(52) U.S. Cl.
CPC ............ *C07F 17/00* (2013.01); *C08F 4/6592* (2013.01); *C08F 4/65908* (2013.01); *C08F 4/65912* (2013.01); *C08F 4/65927* (2013.01); *C08F 10/00* (2013.01); *C08F 110/02* (2013.01)

(58) Field of Classification Search
CPC .... C07F 17/00; C08F 4/65927; C08F 4/6592; C08F 4/65908; C08F 4/65912; C08F 10/00
See application file for complete search history.

(56) References Cited

U.S. PATENT DOCUMENTS

| | | |
|---|---|---|
| 6,451,724 B1 | 9/2002 | Nifant'ev et al. |
| 6,861,485 B2 | 3/2005 | Wang |
| 6,930,156 B2 | 8/2005 | Wang et al. |
| 7,781,549 B2 | 8/2010 | Nagy et al. |
| 7,855,255 B2 | 12/2010 | Chandrashekar et al. |
| 2004/0254310 A1 | 12/2004 | Winslow et al. |
| 2006/0183631 A1 | 8/2006 | Lee et al. |

FOREIGN PATENT DOCUMENTS

| | | |
|---|---|---|
| JP | 3824708 B2 | 9/2006 |
| KR | 10-2004-0090773 A | 10/2004 |
| KR | 10-2006-0031633 A | 4/2006 |
| KR | 10-0753478 B1 | 8/2007 |
| KR | 10-2008-0036989 A | 4/2008 |
| KR | 10-2008-0039479 A | 5/2008 |
| WO | 03/089485 A1 | 10/2003 |

*Primary Examiner* — Caixia Lu
(74) *Attorney, Agent, or Firm* — Dentons US LLP

(57) ABSTRACT

The present invention relates to a transition metal compound that may exhibit high activity in olefin polymerization, and easily control the properties of synthesized olefin polymer such as a chemical structure, molecular weight distribution, a mechanical property, and the like, a catalyst composition comprising the same, and a method for olefin polymerization using the catalyst composition.

10 Claims, No Drawings

METALLOCENE COMPOUNDS, CATALYST COMPOSITIONS COMPRISING THE SAME, AND METHOD FOR PREPARING OLEFIN POLYMERS USING THE SAME

CROSS REFERENCE TO RELATED APPLICATIONS

This application is a National Stage Entry of International Application No. PCT/KR2015/008457, filed on Aug. 12, 2015, and claims the benefit of and priority to Korean Application No. 10-2014-0104498, filed on Aug. 12, 2014, and Korean Patent Application No. 10-2015-0113460, filed on Aug. 11, 2015, all of which are incorporated herein by reference in their entirety for all purposes as if fully set forth herein.

TECHNICAL FIELD

The present invention relates to a novel metallocene transition metal compound, a catalyst composition comprising the transition metal compound, and a method for preparing olefin polymers using the catalyst composition. More specifically, the present invention relates to a transition metal compound that may exhibit high activity in olefin polymerization, and easily control a chemical structure, molecular weight distribution, a mechanical property, and the like of a synthesized olefin polymer, a catalyst composition comprising the same, and a method for olefin polymerization using the catalyst composition.

BACKGROUND OF ART

In the existing commercial preparation process of polyolefins, Ziegler-Natta catalysts such as titanium or vanadium compounds have been widely used. However, although the Ziegler-Natta catalyst has high activity, it is a multi-active-site catalyst, and thus, has a limit in securing desired properties because the molecular weight distribution of the produced polymer is wide and the compositional distribution of comonomers is not uniform.

Thus, recently, metallocene catalysts wherein a transition metal such as titanium, zirconium, hafnium and the like, and a ligand comprising a cyclopentadiene functional group are bonded were developed and are being widely used. The metallocene compound is generally activated with aluminoxane, borane, borate or other activators before use. For example, a metallocene compound having a ligand comprising a cyclopentadienyl group and two sigma chloride ligands uses aluminoxane as an activator. Such a metallocene catalyst is a single-site catalyst having one kind of an active site, and has advantages in that the molecular weight distribution of the produced polymer is narrow, and the molecular weight, stereoregularity, crystallinity, particularly reactivity of comonomers may be largely controlled according to the structures of the catalyst and the ligand. However, since polyolefin polymerized with the metallocene catalyst has low melting point and narrow molecular weight distribution, if applied for certain products, productivity may be remarkably decreased due to the influence of extrusion load and the like, and thus, has difficulty in the practical application. Thus, there have been many attempts to control the molecular weight of polyolefin.

Particularly, in order to overcome the above explained problems of metallocene catalysts, many transition metal compounds coordinated with a ligand compound comprising a hetero atom have been introduced. Specific examples of the transition metal compounds comprising a hetero atom may include azaferrocene compounds having a cyclopentadienyl group comprising a nitrogen atom, a metallocene compound of a structure wherein dialkylamine and a silver functional group are connected as additional chains with a cyclopentadienyl group, or a titanium(IV) metallocene compound having an cyclic alkylamine functional group such as piperidine, and the like.

However, among these, just a few metallocene catalysts are practically applied for a commercial process, and thus, there has been a continuous demand for studies on the metallocene compounds that can be used as a polymerization catalyst capable of realizing higher polymerization performance, and providing medium to low molecular weight polyolefin for processability improvement.

DETAILED DESCRIPTION OF THE INVENTION

Technical Problem

It is an object of the invention to provide a novel transition metal compound that has high activity, and can provide medium to low molecular weight polyolefin in order to improve processability.

It is another object of the invention to provide a catalyst composition comprising the transition metal compound.

It is still another object of the invention to provide a method for preparing an olefin polymer using the catalyst composition.

Technical Solution

The present invention provides a transition metal compound represented by the following Chemical Formula 1.

The present invention also provides a catalyst composition comprising the transition metal compound.

In addition, the present invention provides a method for preparing olefin polymer using the catalyst composition.

Hereinafter, a transition metal compound, a catalyst composition comprising the same, and a method for preparing an olefin polymer using the same according to specific embodiments of the invention will be explained in detail.

One embodiment of the invention provides a transition metal compound represented by the following Chemical Formula 1:

[Chemical Formula 1]

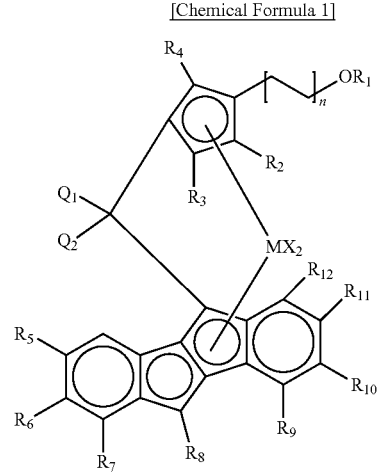

in the Chemical Formula 1, $R_1$ to $R_{12}$ are independently selected from the group consisting of hydrogen, a C1-20 alkyl group, a C2-20 alkenyl group, a C1-20 alkylsilyl group, a C1-20 silylalkyl group, a C1-20 alkoxysilyl group, a C1-20 ether group, a C1-20 silylether group, a C1-20 alkoxy group, a C6-20 aryl group, a C7-20 alkylaryl group and a C7-20 arylalkyl group, or two or more neighboring groups of $R_1$ to $R_{12}$ may be connected to each other to form a substituted or unsubstituted aliphatic or aromatic ring, $Q_1$ and $Q_2$ are independently hydrogen, halogen, a C1-20 alkyl group, a C2-20 alkenyl group, a C1-20 alkoxy group, a C6-20 aryl group, a C2-20 alkoxyalkyl group, a C3-20 heterocycloalkyl group, a C5-20 heteroaryl group, 1-tert-butoxyhexyl, or pivalate, M is Group 4 transition metal, Xs are independently halogen, a C1-20 alkyl group, a C2-20 alkenyl group, a C6-20 aryl group, a nitro group, an amido group, a C1-20 alkylsilyl group, a C1-20 alkoxy group or a C1-20 sulfonate group, and n is an integer of 1 to 10.

The inventors conducted studies on a novel transition metal compound that has high activity, and can provide medium to low molecular weight polyolefin in order to improve processability, and confirmed through experiments that the transition metal compound of the Chemical Formula 1 including a ligand compound of a specific structure bonded to a transition metal has high catalytic activity, can easily control the electronic/steric environment around the transition metal, and thus, can easily control properties of synthesized polyolefin such as a chemical structure, molecular weight distribution, a mechanical property, and the like, and completed the invention.

The transition metal compound of the Chemical Formula 1 is a compound of a Bis-Cp type wherein cyclopentadiene (Cp) and indenoindole are combined, and particularly, functional groups such as an alkyl group, an alkoxy group and the like are introduced into the cyclopentadiene (Cp) group and the indenoindole group, and the transition metal compound may easily control the electronic/steric environment around the transition metal, and thus, exhibits high activity, and can be used to prepare a polyolefin having excellent processability and a mechanical property.

Each substituent in the Chemical Formula 1 will be explained in detail below.

The C1-20 alkyl group may include a linear or branched alkyl group, and the C1-20 alkenyl group and alkynyl group may include linear or branched alkenyl group and alkynl group, respectively.

The aryl group is preferably a C6-20 aromatic ring, and specifically, may include phenyl, naphthyl, anthracenyl, pyridyl, dimethylanilinyl, anisolyl, and the like, but is not limited thereto.

The alkylaryl group means an aryl group, in which one or more C1-20 linear or branched alkyl group is introduced, and the arylalkyl group means a linear or branched alkyl group in which one or more C6-20 aryl group is introduced.

The halogen means fluorine (F), chlorine (Cl), bromine (Br), or iodine (I).

M defined as a Group 4 transition metal may include Ti (titanium), Zr (zirconium), Hf (hafnium), and the like, but is not limited thereto.

And, according to the transition metal compound of one embodiment, $R_1$ in the Chemical Formula 1 may be a C1-20 alkyl group, a C1-20 alkoxy group, or a C6-20 aryl group.

As in the transition metal compound, if a C1-20 alkyl group substituted with a C1-20 alkoxy group is introduced in a cyclopentadiene (Cp) group, the alkyl group substituted with an alkoxy group may form a covalent bond through the interaction with a silanol group on the surface of silica, and thus, compared to the case wherein an alkyl group substituted with an alkoxy group is not introduced or a C1-10 alkyl group that is not substituted with an alkoxy group is introduced in the cyclopentadiene (Cp) group, stable supported polymerization is enabled, and the polymerization activity may be increased. And, the transition metal compound may exhibit very high activity in the olefin polymerization process, when in the cyclopentadiene (Cp) group, particularly $R_1$ is substituted with a C1-20 alkyl group, or a C1-20 alkoxyl group.

And, $R_8$ in the Chemical Formula 1 may be a C1-20 alkyl group, a C1-20 alkoxy group, a C1-20 alkylsilyl group, a C1-20 silylalkyl group, a C6-20 aryl group, or a C7-20 alkylaryl group.

The $R_8$ of the Chemical Formula 1 is a part binding to N of the indenoindole group, and the degree of steric hindrance effect may be controlled according to the kind of substituted functional groups, thus easily controlling the molecular weight of a prepared polyolefin. Particularly, in case $R_8$ is substituted with the above explained functional groups, high activity may be exhibited in an olefin polymerization process, and the properties of prepared polyolefin such as the mechanical property and the like may be easily controlled.

And, in the transition metal compound of one embodiment, it is preferable that $Q_1$ and $Q_2$ are independently a C1-20 alkyl group, a C1-20 alkenyl group, a C1-20 alkoxy group, or a C6-20 aryl group. The $Q_1$ and $Q_2$ correspond to bridge groups connecting the cyclopentadiene (Cp) group and the indenoindole group, and if these positions are substituted with the above explained functional groups, the properties of prepared polyolefin such as the molecular weight distribution and the like may be easily controlled.

Meanwhile, preferable examples of the transition metal compound represented by the Chemical Formula 1 may include compounds of the following Chemical Formulae 11 to 27.

[Chemical Formula 11]

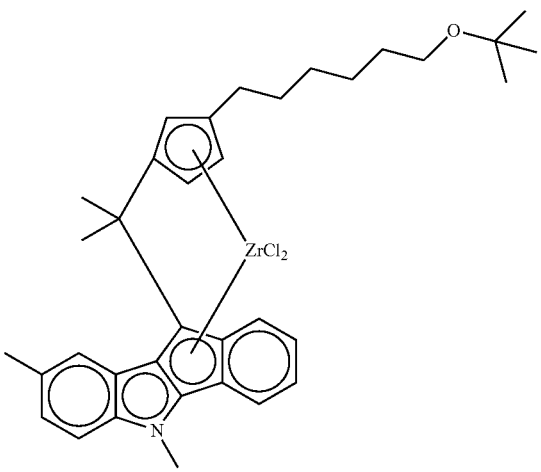

[Chemical Formula 12]
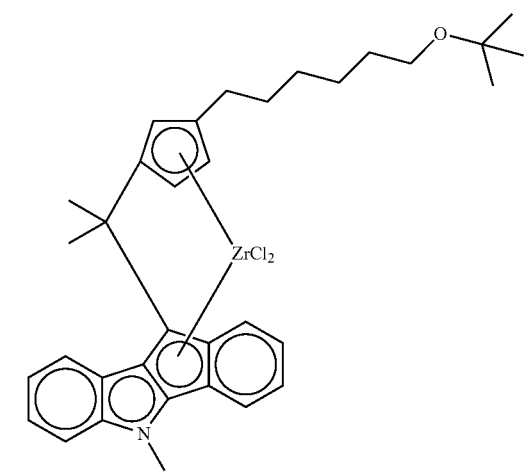
[Chemical Formula 13]
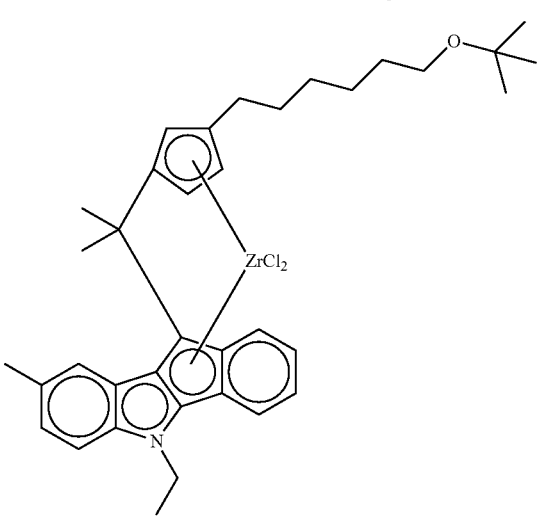
[Chemical Formula 14]
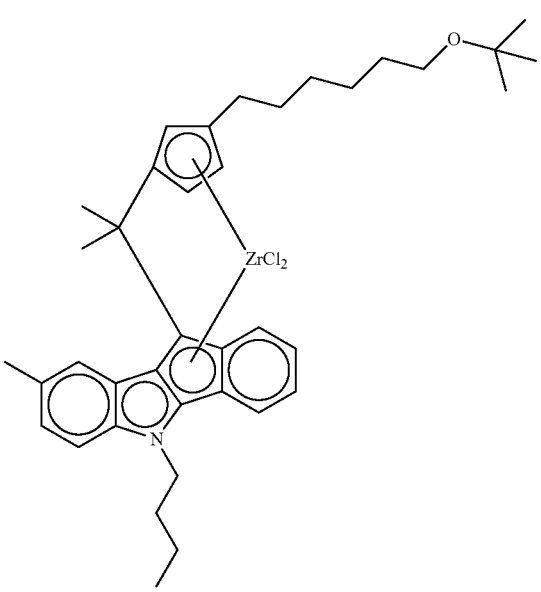
[Chemical Formula 15]
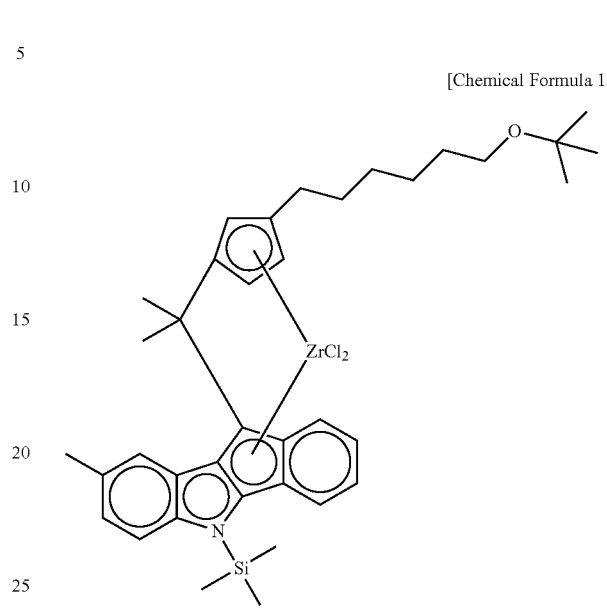
[Chemical Formula 16]
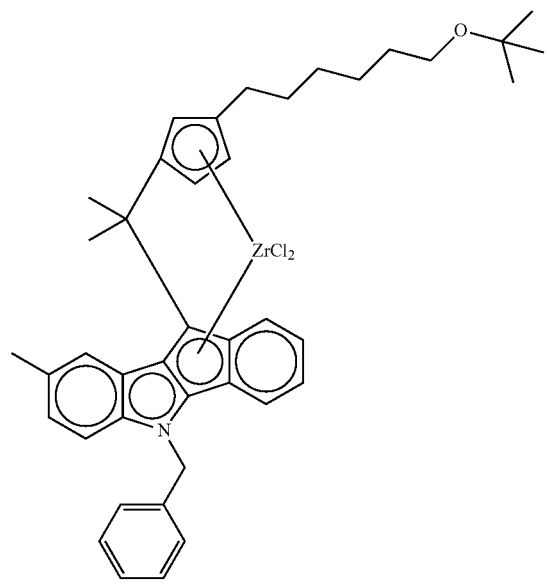

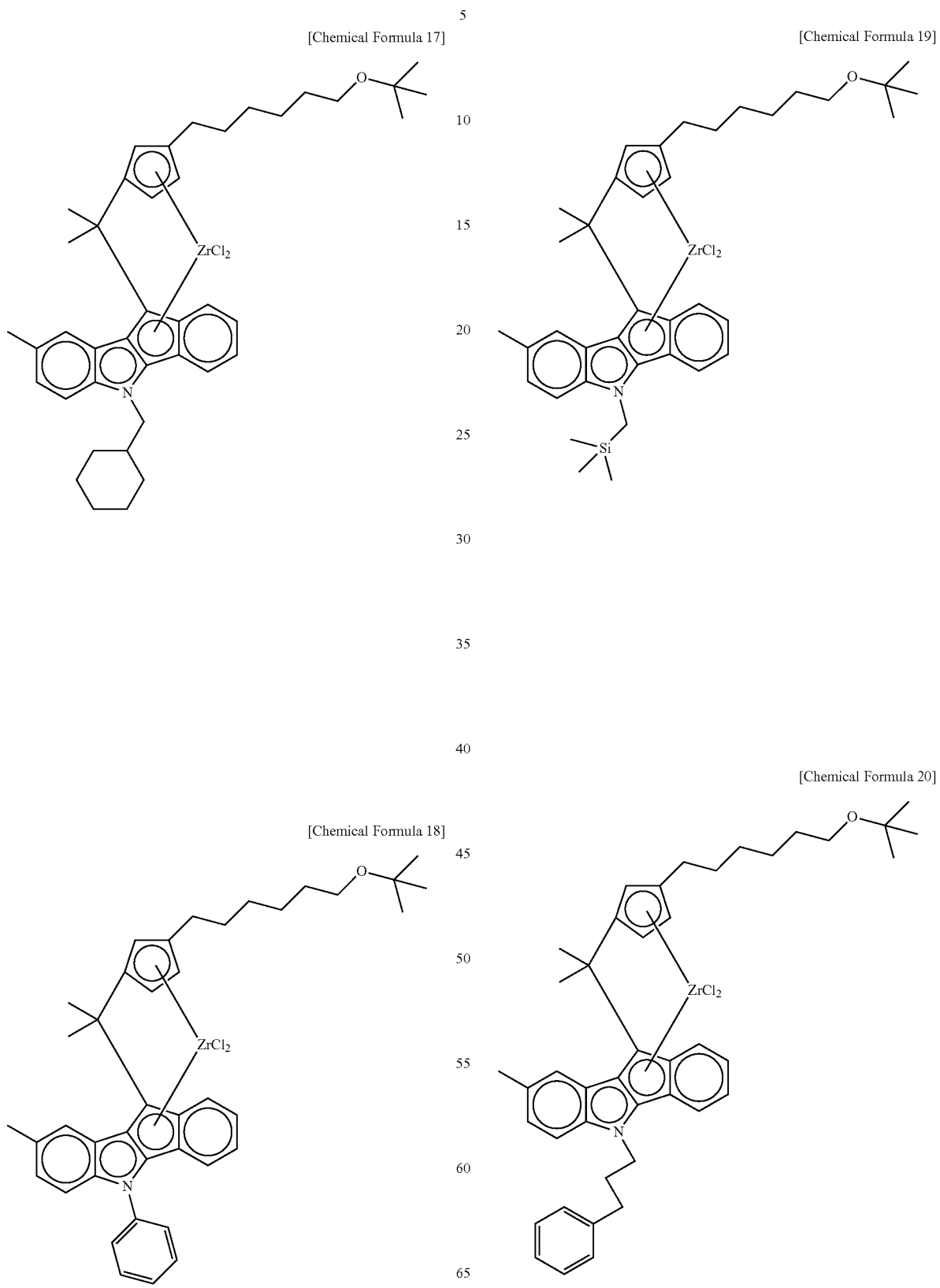

[Chemical Formula 21]
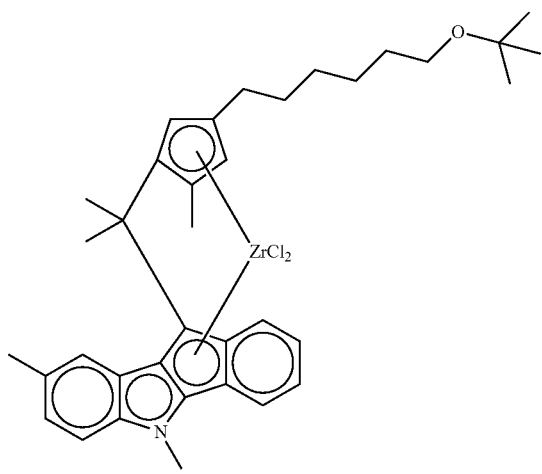
[Chemical Formula 22]
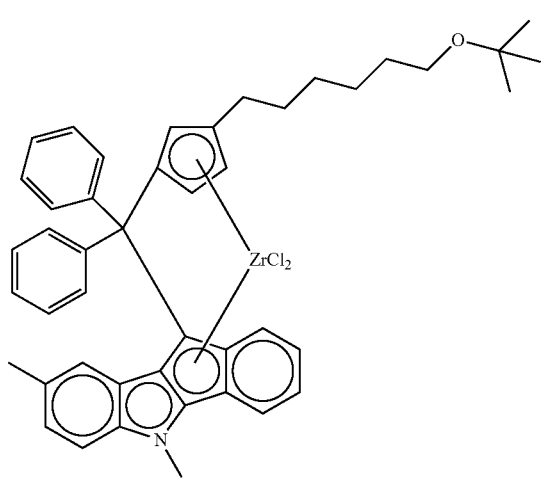
[Chemical Formula 23]
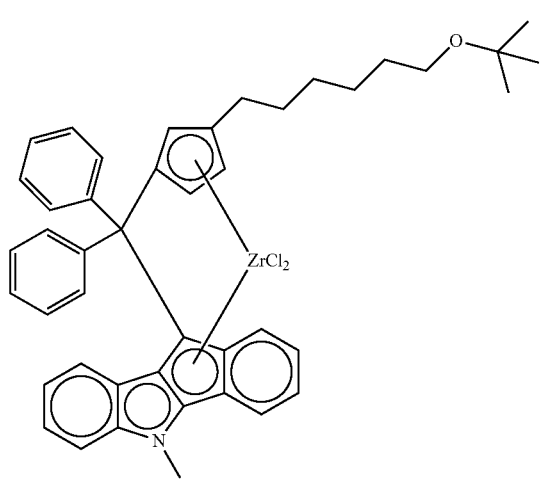
[Chemical Formula 24]
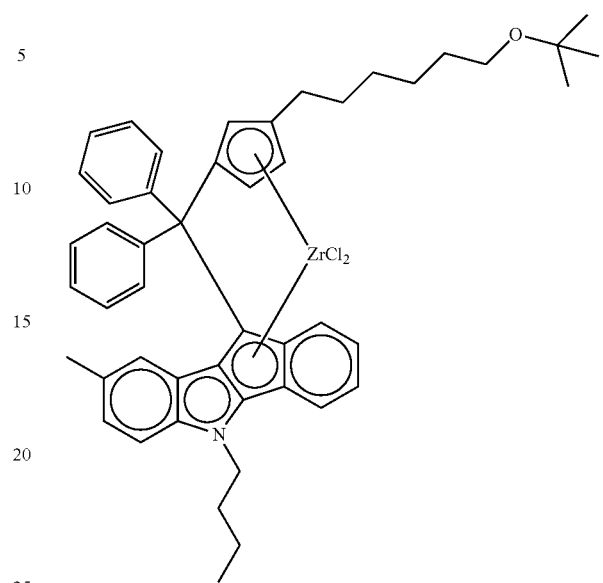
[Chemical Formula 25]
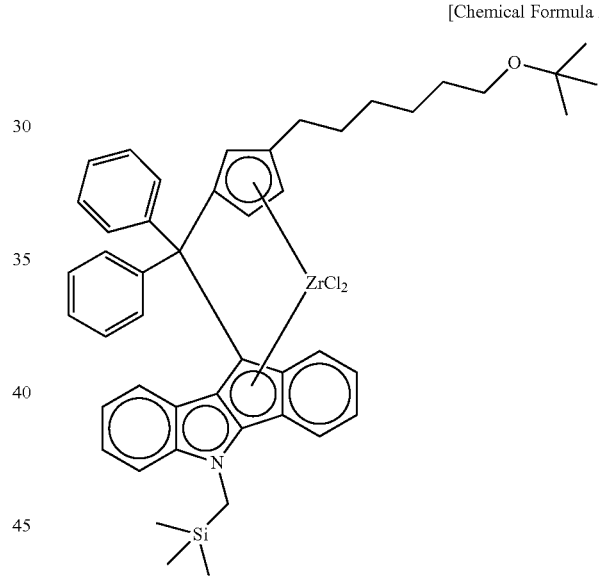
[Chemical Formula 26]
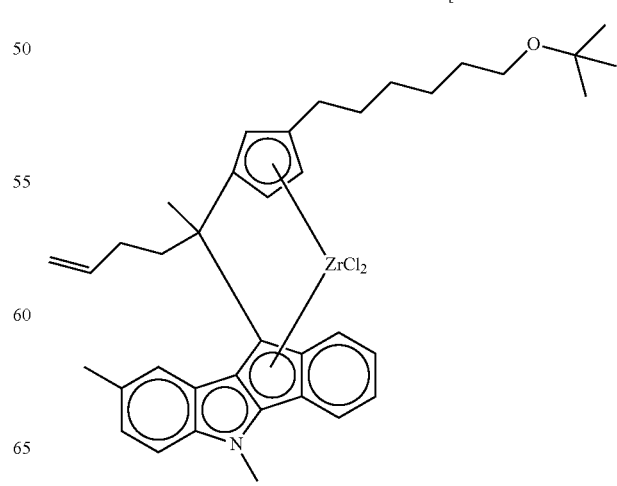

[Chemical Formula 27]

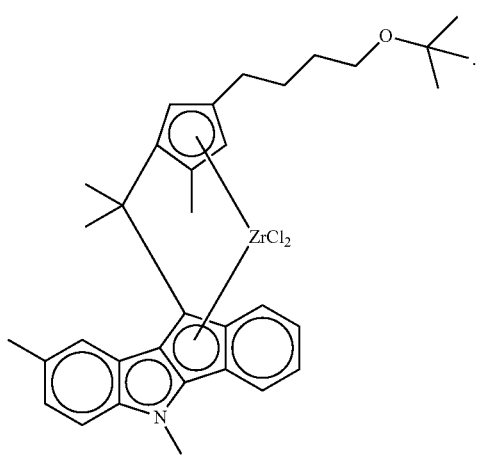

Also, the transition metal compound represented by the Chemical Formula 1 may be formed by reacting a ligand compound synthesized by the method as shown in the following Reaction scheme 1 with a transition metal compound, but is not limited thereto. A method for preparing a compound represented by the Chemical Formula 1 will be specifically explained in the examples described below:

[Reaction scheme 1]

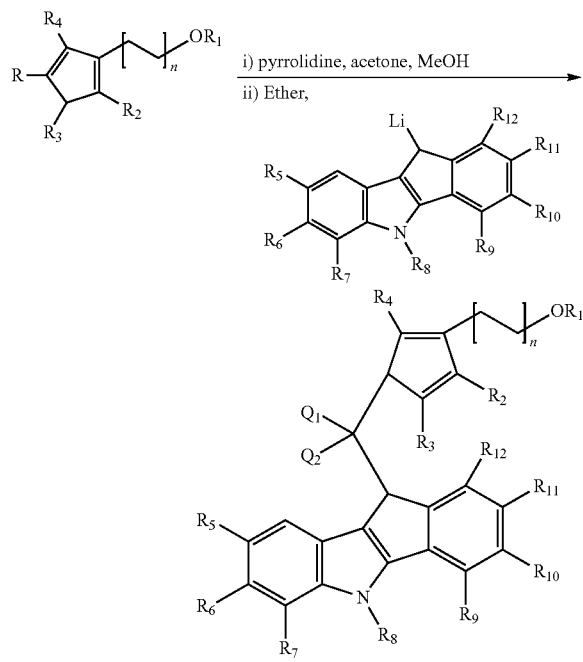

In the Reaction scheme 1, $R_1$ to $R_{12}$, $Q_1$ and $Q_2$, M and X are the same as defined in the Chemical Formula 1, and R is identical to the definitions of $R_1$ to $R_{12}$.

Meanwhile, another embodiment of the invention provides a transition metal catalyst composition comprising the transition metal compound of the Chemical Formula 1 and a cocatalyst.

As mentioned above, if the catalyst composition comprising the transition metal compound of the Chemical Formula 1 is used, properties of synthesized polyolefin such as a chemical structure, molecular weight distribution, a mechanical property, and the like may be easily controlled.

The cocatalyst may include at least one compound selected from the group consisting of the compounds of the following Chemical Formulae 2 to 4.

$$[L\text{-}H]^+[Z(E)_4]^- \text{ or } [L]^+[Z(E)_4]^-$$ [Chemical Formula 2]

in the Chemical Formula 2,
L is neutral or cationic Lewis base,
[L-H]+ or [L]+ is Bronsted acid,
H is a hydrogen atom,
Z is Group 13 element,
Es are independently halogen with hydrogen valence number of 1 or more, a C1-20 hydrocarbyl, a C6-20 aryl group or a C1-20 alkyl group unsubstituted or substituted with alkoxy or phenoxy.

$$D(R_{13})_3$$ [Chemical Formula 3]

in the Chemical Formula 3,
D is aluminum or boron,
$R_{13}$s are independently halogen; a C1-20 hydrocarbyl group; or a C1-20 hydrocarbyl group substituted with halogen.

[Chemical Formula 4]

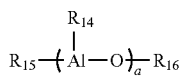

in the Chemical Formula 4,
$R_{14}$, $R_{15}$ and $R_{16}$ are independently hydrogen; halogen; a C1-20 hydrocarbyl group; or a C1-20 hydrocarbyl group substituted with halogen, and a is an integer of 2 or more.

In the Chemical Formulae 2 and 3, "hydrocarbyl" is a monovalent functional group formed by removing hydrogen atom from hydrocarbon, and may include ethyl, phenyl and the like.

Also, the catalyst composition may further comprise a solvent, in addition to the transition metal compound represented by the Chemical Formula 1; and a cocatalyst comprising at least one selected from the group consisting of the compounds of the Chemical Formulae 2 to 4.

As the solvent, those known to be used in a transition metal catalyst composition may be used without specific limitations, and for example, aliphatic hydrocarbon solvents such as pentane, hexane, heptane, nonane, decane and derivatives thereof; aromatic hydrocarbon solvents such as toluene, xylene, benzene; or hydrocarbon solvents substituted with a chlorine atom such as dichloromethane, chlorobenzene, and the like may be used. The content of the solvent in the catalyst composition may be appropriately controlled according to the properties of the catalyst composition used and the conditions of the preparation process of olefin polymer applied.

The catalyst composition may be in the form wherein the transition metal compound and the cocatalyst compound are supported in a carrier. The catalyst composition supported in the carrier may be easily applied for gas phase or suspension polymerization, and may be applied for a polyolefin polymerization process more economically and efficiently due to high productivity of prepared polyolefin.

As the carrier, those known to be commonly used in a catalyst for preparing olefin polymer may be used without specific limitations. For example, as the carrier, silica, alumina, magnesia or a mixture thereof may be used, and the carrier may be dried at high temperature, and commonly include oxide such as $Na_2O$, $K_2CO_3$, $BaSO_4$ and $Mg(NO_3)_2$, carbonate, sulfate, nitrate and the like.

Another embodiment of the invention provides a method for preparing a polyolefin, comprising a step of polymerizing olefin monomers in the presence of the catalyst composition.

As explained above, since the transition metal compound of the Chemical Formula 1 may easily control the electronic/steric environment around the metal, it may easily control the properties of synthesized polyolefin such as a chemical structure, molecular weight distribution, a mechanical property, and the like.

For the polymerization reaction of olefin monomers, polymerization processes known to be used for polymerization of olefin monomers such as a continuous solution polymerization process, a bulk polymerization process, a suspension polymerization process, a slurry polymerization process or an emulsion polymerization process may be used without limitations.

Examples of the olefin monomers that can be polymerized using the transition metal compound and the cocatalyst may include ethylene, alpha-olefin, cyclic olefin and the like, and diene olefin monomers or triene olefin monomers and the like having two or more double bonds may also be polymerized. Specific examples of the monomer may include ethylene, propylene, 1-butene, 1-pentene, 4-methyl-1-pentene, 1-hexene, 1-heptene, 1-octene, 1-decene, 1-undecene, 1-dodecene, 1-tetradecene, 1-hexadecene, 1-eicosene, norbornene, norbornadiene, ethylidenenorbornene, phenylnorbornene, vinylnorbornene, dicylcopentadiene, 1,4-butadiene, 1,5-pentadiene, 1,6-hexadiene, styrene, alpha-methylstyrene, divinylbenzene, 3-chloromethylstyrene, and the like, and a mixture of two or more kinds of these monomers may also be copolymerized. In case the polyolefin is copolymer of ethylene with another comonomer, the monomer constituting the copolymer may be preferably at least one selected from the group consisting of propylene, 1-butene, 1-hexene, 4-methyl-1-pentene, and 1-octene.

Advantageous Effects

According to the present invention, a transition metal compound that may exhibit high activity in an olefin polymerization reaction, and may easily control the properties of synthesized olefin polymer such as a chemical structure, molecular weight distribution, a mechanical property and the like, a catalyst composition comprising the same, and a method for preparing an olefin polymer using the catalyst composition are provided.

DETAILED DESCRIPTION OF THE EMBODIMENTS

Hereinafter, the present invention will be explained in detail with reference to the following examples. However, these examples are only to illustrate the invention and the scope of the invention is not limited thereto.

In the examples, comparative examples and experimental examples described below, organic reagents and solvent were purchased from Aldrich Company and Merck Company, and purified by standard methods before use. In all steps of synthesis, contact with air and moisture was blocked to increase reproducibility of experiments. Also, in order to prove the structure of compounds, spectrum was obtained using 500 MHz nuclear magnetic resonance (NMR).

Example: Synthesis of Ligand Compounds and Transition Metal Compounds

Example 1: Synthesis of [(10-(2-(3-(6-tert-butoxyhexyl)cyclopenta-2,4-dienyl)propan-2-yl)-5,8-dimethyl-5,10-dihydroindeno[1,2-b]indole)]zirconium chloride (1) Synthesis of a Ligand Compound (10-(2-(3-(6-tert-butoxyhexyl)cyclopenta-2,4-dienyl)propan-2-yl)-5,8-dimethyl-5,10-dihydroindeno[1,2-b]indole)

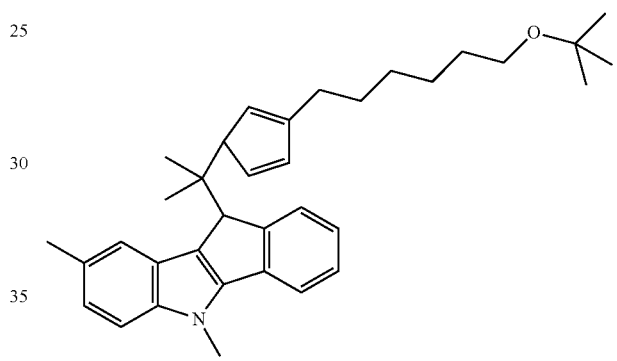

Into a dried 250 mL Schlenk flask, 5.25 g (23.6 mmol) of 2-(6-tert-butoxyhexyl)cyclopenta-1,3-diene was introduced, 50 ml of methanol and 4 ml of acetone were added, and then, the mixture was cooled to 0° C. And 2.95 ml of pyrrolidine (1.5 equivalents) was added dropwise, and the temperature of the reaction mixture was slowly raised to room temperature, and then, the mixture was stirred for 7 hours, 50 ml of water was introduced in the flask to quench, and an organic layer was separated and dried over $MgSO_4$. It was confirmed through NMR that 5.0 g (19.07 mmol, 80.7%) of 2-(6-tert-butoxyhexyl)-5-(propan-2-ylidene)cyclopenta-1,3-diene was produced.

Simultaneously, into a dried 250 mL flask, 2.33 g (10 mmol) of indenoindole was introduced, and argon atmosphere was formed, and then, 50 ml of ether was introduced under reduced pressure to dissolve. And the solution was cooled to 0° C., and then, 4.8 ml (12 mmol) of a 2.5M n-BuLi hexane solution was added dropwise to raise the temperature to room temperature, and then, the solution was stirred for one day.

Next, the above prepared 2-(6-tert-butoxyhexyl)-5-(propan-2-ylidene)cyclopenta-1,3-diene was dissolved in ether, and then, the lithiated indenoindole solution was added dropwise to the ether solution, followed by stirring for one day. Thereafter, into the flask, about 50 ml of water was introduced to quench, and then, an organic layer was separated and dried over $MgSO_4$, and filtered to obtain a pure organic solution. And the solvent was completely evaporated from the solution under vacuum condition to obtain 4.7 g (0.48 mmol, 94.8%) of black oil.

$^1$H-NMR (500 MHz, CDCl$_3$): 0.87, 1.17, 1.27, 1.34 (6H, m), 1.20 (9H, s), 1.44 (4H, m), 1.54 (2H, m), 1.54-1.69 (4H, m), 2.42, 2.48 (3H, s), 3.35 (2H, m), 4.03 (3H, m), 5.73, 6.01, 6.05, 6.13, 6.61 (3H, s), 6.97-7.04 (2H, m), 7.07-7.18 (2H, m), 7.32 (1H, m), 7.55-7.63 (2H, m).

(2) Synthesis of a Transition Metal Compound ([(10-(2-(3-(6-tert-butoxyhexyl)cyclopenta-2,4-dienyl)propan-2-yl)-5,8-dimethyl-5,10-dihydroindeno[1,2-b]indole)]zirconium chloride)

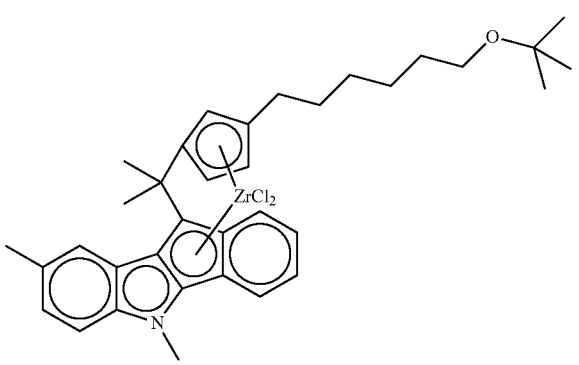

Into an oven-dried 250 mL Schlenk flask, the ligand prepared in (1) was introduced, 4 equivalents of MTBE and a Tol solution were dissolved in a solvent, and then, 2.1 equivalents of a nBuLi solution was added, and the solution was lithiated until the next day.

Then, in a glove box, 2.1 equivalents of ZrCl$_4$(THF)$_2$ was taken and put in a 250 ml Schlenk flask, and ether was introduced to prepare a Zr suspension.

Both flasks were cooled to −78° C., and then, ligand anion was slowly added to the Zr suspension. Thereafter, the temperature of the reaction mixture was slowly raised to room temperature, and the mixture was stirred for one day, and then, ether in the mixture was removed to about ⅕ volume through vacuum suction, and hexane of the volume of about 5 times of the remaining solvent was added. Wherein, since the synthesized catalyst precursor has low solubility to hexane, crystallization may be promoted by adding hexane. The hexane slurry was filtered under argon, and both the filtered solid and the filtrate were evaporated under vacuum. The filter cake remaining at the top and the filtrate were respectively confirmed through NMR as to whether or not catalyst was synthesized, and then, they were weighed in a glove box, and sampled to confirm yield and purity. From 4.7 g (9.5 mmol) of ligand, 9.35 mmol (98.7% yield) of purple catalyst precursor was obtained. Both the filtrate and the filter cake were confirmed as catalyst precursors, and 1.737 g of the purple solid and 2.96 g were dissolved in toluene to obtain 10.96 g of a toluene solution.

NMR based purity (wt %)=64.3% (Filter cake), 100% (filtrate). MW=655.85

$^1$H-NMR (500 MHz, CDCl$_3$): 0.81 (2H, m), 1.13 (9H, d), 1.22 (2H, m), 1.32 (2H, m), 1.43 (4H, m), 2.34 (3H, d), 2.49 (6H, t), 3.23 (2H, m), 4.14 (3H, s), 5.09, 5.35, 5.45, 5.69, 5.86, 6.01 (3H, s), 6.99 (1H, m), 7.32 (3H, m), 7.74 (1H, q), 7.94 (1H, d), 7.97 (1H, d).

Comparative Example 1: Synthesis of [(10-(cyclopenta-2,4-dienyldiphenylmethyl)-5,8-dimethyl-5,10-dihydroindeno[1,2-b]indole)]zirconium chloride (1) Synthesis of a Ligand Compound (10-(cyclopenta-2,4-dienyldiphenylmethyl)-5,8-dimethyl-5,10-dihydroindeno[1,2-b]indole)

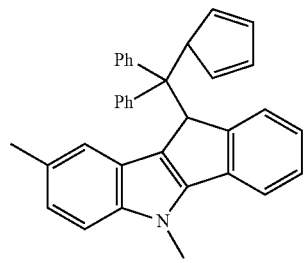 [SMILES: Cc1ccc2c(c1)c1c(n2C)-c2ccccc2C1C(c1ccccc1)(c1ccccc1)C1C=CC=C1]

Into a dried 250 mL Schlenk flask, benzophenone (3.65 g, 20 mmol) was introduced, and dissolved in 50 ml of THF. The solution was cooled to 0° C., 20 ml (2.0M in THF) of a NaCp solution was slowly added, and then, the mixture was stirred for 1 hour while gradually raising the temperature. After the reaction was completed, 20 ml of water was introduced to quench remaining NaCp, and an organic layer was extracted with 50 ml of ether and vacuum dried at low temperature. The concentrate was filtered through a silica filter using hexane as eluent, and the filtrate was dried to obtain fulvene compound in the form of red flake at 80% yield. $^1$H-NMR (500 MHz, CDCl$_3$): 6.30 (2H, m), 6.60 (2H, m), 7.32-7.40 (10H, m).

And, among them, 2.3 g (10 mmol) was taken and reacted with 10 mmol of the lithiated indenoinidole in a THF solution for one day to obtain a purple ligand compound in the form of oil. $^1$H-NMR (500 MHz, CDCl$_3$): 2.27 (3H, m), 3.84 (3H, m), 3.98 (1H, s), 5.40 (1H, s), 6.33-6.80 (4H, m), 6.87-6.95 (3H, m), 7.11-7.44 (12H, m), 7.56 (1H, m), 7.82 (1H, m).

(2) Synthesis of a Transition Metal Compound ([(10-(cyclopenta-2,4-dienyldiphenylmethyl)-5,8-dimethyl-5,10-dihydroindeno[1,2-b]indole)]zirconium chloride)

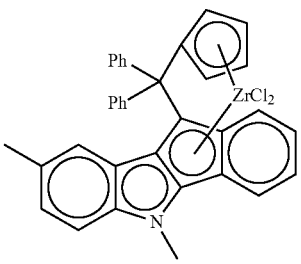

3.3 g (7.1 mmol) of the ligand prepared in (1) was dissolved in 60 ml of anhydrous ether, and then, 7.4 ml (18.5 mmol) of a 2.5M nBuLi hexane solution was slowly added thereto. And, the reaction mixture was stirred for one day, and slowly added to a slurry of 2.6 g (7.1 mmol) of ZrCl$_4$(THF)$_2$ dispersed in 40 ml of ether at −78° C., and then, the temperature was raised, and the mixture was additionally reacted for one day. After the reaction, ether was vacuum dried to ¼ volume, hexane was filled with the reduced volume to produce precipitate, which was filtered to obtain a red purple solid remaining at the top of the filter.

¹H-NMR (500 MHz, CDCl₃): 2.09 (3H, s), 4.20 (3H, s), 5.00 (1H, s), 5.53 (1H, s), 5.89 (1H, s), 6.29 (1H, s), 6.42 (2H, m), 6.78 (1H, m), 7.14 (2H, m), 7.27-7.46 (8H, m), 7.57 (2H, m), 7.95-7.99 (2H, m), 8.04-8.06 (3H, m).

Comparative Example 2: Synthesis of [10-(1-(cyclopenta-2,4-dien-1-yl)cyclohexyl)-5,8-dimethyl-5,10-dihydroindeno[1,2-b]indole]zirconium chloride (1) Synthesis of a Ligand Compound 10-(1-(cyclopenta-2,4-dien-1-yl)cyclohexyl)-5,8-dimethyl-5,10-dihydroindeno[1,2-b]indole

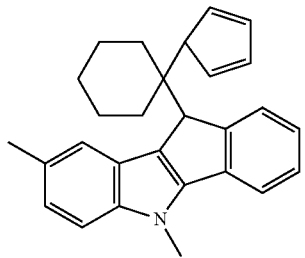 [SMILES: Cc1ccc2c(c1)c1c(n2C)-c2ccccc2C1C1(C2C=CC=C2)CCCCC1]

Into a dried 250 mL Schlenk flask, cyclohexanone (1.963 g, 20 mmol) was introduced, and dissolved in 50 ml of THF. The solution was cooled to 0° C., 20 ml (2.0M in THF) of a NaCp solution was slowly added, and then, the mixture was stirred for 1 hour while gradually raising the temperature. After the reaction was completed, 20 ml of water was introduced to quench remaining NaCp, and an organic layer was extracted with 50 ml of ether and vacuum dried at low temperature. The concentrate was filtered through a silica filter using hexane as eluent, and the filtrate was dried to obtain fulvene compound in the form of red flake at 80% yield. And 20 mmol of Indenoindole was dissolved in 50 ml of a THF solution. The solution was cooled to 0° C., 8 ml of n-BuLi was introduced to progress lithiation for one day, and the lithiated solution was reacted with the above fulvene compound to obtain a ligand in the form of oil.

¹H-NMR (500 MHz, CDCl₃): 7.65 (2H, m), 7.39-7.46 (3H, m), 6.50-6.48 (4H, m), 3.82 (3H, s), 3.76 (1H, 2), 2.58 (1H, t), 2.43 (3H, s), 1.43-1.53 (10H, m).

(2) Synthesis of a Transition Metal Compound [10-(1-(cyclopenta-2,4-dien-1-yl)cyclohexyl)-5,8-dimethyl-5,10-dihydroindeno[1,2-b]indole]zirconium chloride

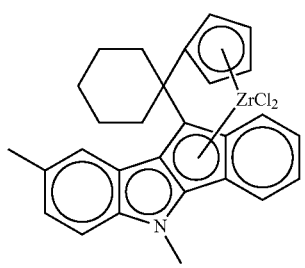

10 mmol of the ligand prepared in (1) was dissolved in 60 ml of anhydrous ether, and then, 8.4 ml (21 mmol) of a 2.5M nBuLi hexane solution was slowly added thereto. And, the reaction mixture was stirred for one day, and slowly added to a slurry of 3.66 g (10 mmol) ZrCl₄(THF)₂ dispersed in 40 ml ether at −78° C., and then, the temperature was raised, and the mixture was additionally reacted for one day. After the reaction, ether was vacuum dried to ¼ volume, and hexane was filled with the reduced volume to produce precipitate, which was filtered to obtain a red solid at the top of the filer.

¹H-NMR (500 MHz, CDCl₃): 7.66 (2H, m), 7.44 (3H, m), 7.28 (1H, m), 6.51 (2H, m), 3.82 (3H, s), 2.45 (3H, s), 1.43-1.53 (10H, m).

EXPERIMENTAL EXAMPLE

Experimental Example 1: Preparation of ethylene homopolymer

A 600 mL Parr reactor was vacuum dried at 120° C. for 1 hour, and argon was added thereto while lowering the temperature to 50° C. Under argon atmosphere, a hexane solvent (400 mL) and 0.46 g of a TEAL cocatalyst were introduced into the reactor using a cannula. And, in order prevent fouling, 0.17 ml of an antistatic agent (ASA) was introduced using a syringe, and the mixture was stirred for 5 minutes. Thereafter, 10 mg of the transition metal compound prepared in Example 1 or Comparative Example 1 was introduced into the reactor, and argon was removed in the reactor. The temperature was raised to 80° C., and then, while introducing 40 bar of ethylene into the reactor, the mixture was stirred at 500 rpm for 60 minutes to conduct a polymerization reaction. After the polymerization reaction, the temperature was lowered to 60° C., pressure in the reactor was removed, and the reactor and the stirrer were separated, and then, polymerized polymer was put in a flask (1 L beaker). And, the polymer was filtered using an aspirator, and then, the polymer was dried in an oven, and the properties were measured.

The properties of the ethylene homopolymers prepared using the transition metal compounds of example and comparative examples are shown in the following Table 1.

TABLE 1

| | Support Recipe | | | | |
| --- | --- | --- | --- | --- | --- |
| | MAO (60° C.) mmol/g-SiO₂ | Met (40° C.) mmol/g-SiO₂ | Catalytic activity (kgPE/g · cat) | Molecular weight | PDI |
| Example 1 | 8 | 0.1 | 5.9 | 237,000 | 2.4 |
| Comparative Example 1 | 8 | 0.1 | 0.4 | 481,000 | 2.5 |
| Comparative Example 2 | 8 | 0.1 | 0.7 | 442,000 | 2.4 |

From the Table 1, it was confirmed that the catalyst prepared in Example 1 has remarkably higher activity than those of comparative examples. And, since the polyolefin prepared using the catalyst of example exhibits medium to low molecular weight, it is expected that the limitation of the metallocene catalysts of the prior art that could not easily prepare medium to low molecular weight polyolefins may be overcome, and processability may be improved.

The invention claimed is:

1. A transition metal compound represented by the following Chemical Formula 1:

[Chemical Formula 1]

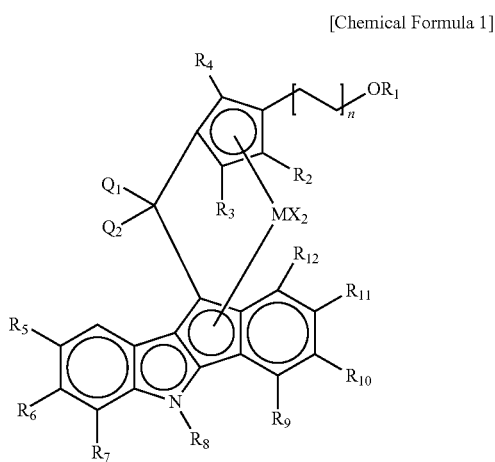

in the Chemical Formula 1, $R_1$ to $R_{12}$ are independently selected from the group consisting of hydrogen, a C1-20 alkyl group, a C2-20 alkenyl group, a C1-20 alkylsilyl group, a C1-20 silylalkyl group, a C1-20 alkoxysilyl group, a C1-20 ether group, a C1-20 silylether group, a C1-20 alkoxy group, a C6-20 aryl group, a C7-20 alkylaryl group and a C7-20 arylalkyl group, or two or more neighboring groups of $R_1$ to $R_{12}$ are optionally connected with each other to form a substituted or unsubstituted aliphatic or aromatic ring, $Q_1$ and $Q_2$ are independently hydrogen, halogen, a C1-20 alkyl group, a C2-20 alkenyl group, a C1-20 alkoxy group, a C6-20 aryl group, a C2-20 alkoxyalkyl group, a C3-20 heterocycloalkyl group, a C5-20 heteroaryl group, 1-tert-butoxyhexyl, or pivalate, M is Group 4 transition metal, Xs are independently halogen, a C1-20 alkyl group, a C2-20 alkenyl group, a C6-20 aryl group, a nitro group, an amido group, a C1-20 alkylsilyl group, a C1-20 alkoxy group or a C1-20 sulfonate group, and n is an integer of 1 to 10.

2. The transition metal compound according to claim 1, wherein M is selected from the group consisting of Ti, Zr and Hf.

3. The transition metal compound according to claim 1, wherein $R_1$ is a C1-20 alkyl group, a C1-20 alkoxyl group, or a C6-20 aryl group.

4. The transition metal compound according to claim 1, wherein $R_8$ is a C1-20 alkyl group, a C1-20 alkoxy group, a C1-20 alkylsilyl group, a C1-20 silylalkyl group, a C6-20 aryl group, or a C7-20 alkylaryl group.

5. The transition metal compound according to claim 1, wherein $Q_1$ and $Q_2$ are independently a C1-20 alkyl group, a C1-20 alkenyl group, a C1-20 alkoxy group, or a C6-20 aryl group.

6. A catalyst composition comprising the transition metal compound represented by the Chemical Formula 1 according to claim 1; and a cocatalyst comprising at least one selected from the group consisting of the following Chemical Formulae 2 to 4:

$$[L-H]^+[Z(E)_4]^- \text{ or } [L]^+[Z(E)_4]^- \quad \text{[Chemical Formula 2]}$$

in the Chemical Formula 2,

L is neutral or cationic Lewis base, $[L-H]^+$ or $[L]^+$ is Bronsted acid,

H is a hydrogen atom,

Z is Group 13 element,

Es are independently halogen with hydrogen valence number of 1 or more, a C1-20 hydrocarbyl, a C6-20 aryl group or a C1-20 alkyl group unsubstituted or substituted with alkoxy or phenoxy, $$D(R_{13})_3 \quad \text{[Chemical Formula 3]}$$

in the Chemical Formula 3,

D is aluminum or boron, $R_{13}$s are independently halogen; a C1-20 hydrocarbyl group; or a C1-20 hydrocarbyl group substituted with halogen,

[Chemical Formula 4]

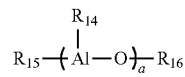

in the Chemical Formula 4, $R_{14}$, $R_{15}$ and $R_{16}$ are independently hydrogen; halogen; a C1-20 hydrocarbyl group; or a C1-20 hydrocarbyl group substituted with halogen, and a is an integer of 2 or more.

7. The catalyst composition according to claim 6, further comprising a solvent.

8. The catalyst composition according to claim 6, wherein the transition metal compound and the cocatalyst are supported in a carrier.

9. A method for preparing an olefin polymer, comprising a step of polymerizing olefin monomers in the presence of the catalyst composition according to claim 6.

10. The method according to claim 9, wherein the olefin monomer includes at least one selected from the group consisting of ethylene, propylene, 1-butene, 1-penten, 4-methyl-1-penten, 1-hexene, 1-heptene, 1-octene, 1-decene, 1-undecene, 1-dodecene, 1-tetradecene, 1-hexadecene, 1-eicosene, norbornene, norbornadiene, ethylidene norbornene, phenyl norbornene, vinyl norbornene, dicyclopentadiene, 1,4-butadiene, 1,5-pentadiene, 1,6-hexadiene, styrene, alpha-methylstyrene, divinylbenzene and 3-chloromethylstyrene.

* * * * *